US 6,629,961 B1

(12) United States Patent
Israelsson et al.

(10) Patent No.: US 6,629,961 B1
(45) Date of Patent: *Oct. 7, 2003

(54) MEDICAL DEVICE WITH HYDROPHILIC COATING

(75) Inventors: Anette Israelsson, Göteborg (SE); Jan Utas, Kungsbacka (SE)

(73) Assignee: Astra Aktiebolag, Sodertalje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/875,204

(22) PCT Filed: Jun. 19, 1997

(86) PCT No.: PCT/SE97/01121

§ 371 (c)(1),
(2), (4) Date: Jul. 31, 1997

(87) PCT Pub. No.: WO97/49437

PCT Pub. Date: Dec. 31, 1997

(65) Prior Publication Data
(65)

(30) Foreign Application Priority Data

Jun. 26, 1996 (SE) ............................... 9602529

(51) Int. Cl.⁷ ................................. A61M 5/32
(52) U.S. Cl. .................................... 604/265
(58) Field of Search .......... 604/96, 265, 264; 128/898; 428/423.1; 427/2.1, 2.12, 2.13, 2.3; 424/443

(56) References Cited

U.S. PATENT DOCUMENTS

| 4,154,244 A | * | 5/1979 | Becker et al. .......... 128/349 B |
| 4,373,009 A | * | 2/1983 | Winn |
| 4,481,323 A | * | 11/1984 | Sterling ...................... 524/269 |
| 4,585,666 A | * | 4/1986 | Lambert |
| 4,666,437 A | * | 5/1987 | Lambert ...................... 604/265 |
| 4,906,237 A | * | 3/1990 | Johansson et al. .......... 604/265 |
| 5,160,559 A | * | 11/1992 | Scovil et al. ............... 156/73.6 |
| 5,160,790 A | * | 11/1992 | Elton ......................... 428/412 |
| 5,385,152 A | * | 1/1995 | Abele et al. ................. 600/585 |
| 5,756,144 A | * | 5/1998 | Wolff et al. .................. 427/2.3 |
| 5,776,611 A | * | 7/1998 | Elton et al. .............. 428/423.1 |
| 5,849,843 A | | 12/1998 | Laurin et al. ................. 525/66 |

FOREIGN PATENT DOCUMENTS

| EP | 0483941 | 5/1992 |
| EP | 0566755 | 10/1993 |
| EP | 0592870 | 4/1994 |
| EP | 0093093 | 11/1998 |
| WO | 9523619 | 9/1995 |

* cited by examiner

Primary Examiner—Michael J. Hayes
(74) Attorney, Agent, or Firm—White & Case LLP

(57) ABSTRACT

Method for the manufacture of a medical device which presents a hydrophilic surface coated elongate shaft for insertion into a body passageway comprising the steps of having the elongate shaft formed from a thermoplastic elastomer material selected from the group consisting of a polyether block amide and a styrene block copolymer and forming the hydrophilic coating on the elongate shaft by applying sequentially to the surface of the elongate shaft a solution comprising between 0.05 to 40% (weight to volume) of an isocyanate compound and a solution containing between 0.5 and 50% (weight to volume) of polyvinylpyrrolidone and curing at an elevated temperature.

15 Claims, No Drawings

MEDICAL DEVICE WITH HYDROPHILIC COATING

The present invention relates to medical devices which present an elongate shaft having an outer surface coating for insertion into a passageway in a human or animal body and is principally, but not exclusively, concerned with surface coated catheters.

Many medical devices incorporate elongate shafts such as tubes which are intended for insertion into and through passageways of a living body such as those of the urethral tract and the cardiovascular system. The most common type of this general grouping of medical devices are known as catheters. Exemplary catheters include those designated for urological, angioplasty and valvuloplasty uses, that is, adapted respectively for insertion into the urethra, the lumen of a blood vessel and heart passageway of a living body, normally a human body.

Because of the intended use of such medical devices certain parameters need to be satisfied by the material from which the elongate shaft is manufactured. The material must fulfil such requirements as softness, good kink resistance, good dimensional stability, processability, for example ease to form and glue, and the possibility to be sterilised by radiation, steam, ethylene oxide or other means. There is further the need for the material to accept a surface treatment which will impart desired surface properties to the medical device such as lubricity, hydrophilicity and blood compatibility. To this latter end, the chemistry of the substrate material is critical since this affects the possibility to coat the substrate.

For many years now polyvinyl chloride (PVC) has been used to manufacture medical devices having elongate shafts for insertion into a body passageway such as catheters due to PVC fulfilling the requirements mentioned in the preceding paragraph.

For instance, prior European patent application publication No. 0093093 (Astra Meditec. AB) makes known a process for manufacturing a PVC urinary catheter having a hydrophilic outer surface coating which exhibits a low coefficient of friction when wetted. The process involves forming a hydrophilic surface coating on the PVC catheter by sequentially applying a solution containing between 0.05–40% (weight/volume, that is, kg/l) of an isocyanate compound and a solution of polyvinylpyrrolidone (PVP) containing between 0.5–50% (weight/volume) to the outer surface of the catheter, for example by dipping, and then curing the hydrophilic coating at an elevated temperature advantageously in the presence of a water-containing gas such as ambient air.

The suitability of PVC for medical devices such as catheters, however, is now being questioned on environmental grounds and further because of the toxicity of the plasticisers added to PVC. Moreover, coating PVC catheters by, for example, the process of European patent application publication No. 0093093 results in an appreciable shrinkage of the PVC catheters in the longitudinal direction, typically 6–7% of the original length, due to the operating temperatures used in the coating process. The obvious disadvantage of such appreciable shrinkage is the wastage of material in the sense that PVC catheters of longer length than finally required have to be used to account for the shrinkage. In addition, quality control of the coating process is made more complicated than would be ideal by this marked degree of shrinkage.

There is therefore a need for a medical device which presents a hydrophilic surface coated. non-PVC elongate shaft for insertion into a body passageway which experiences no appreciable shrinkage on application of the hydrophilic surface coating.

To this end, the present invention provides a method for the manufacture of a medical device which presents a hydrophilic surface coated elongate shaft for insertion into a body passageway comprising the steps of having the elongate shaft formed from a thermoplastic elastomer material selected from the group consisting of a polyether block amide and a styrene block copolymer and forming the hydrophilic coating on the elongate shaft by applying sequentially to the surface of the elongate shaft a solution comprising between 0.05 to 40% (weight to volume) of an isocyanate compound and a solution containing between 0.5 and 50% (weight to volume) of polyvinylpyrrolidone and curing at an elevated temperature.

The use of a polyether block amide or a styrene block copolymer results in an elongate shaft which undergoes substantially no shrinkage in the longitudinal direction as compared to PVC on application of the hydrophilic coating as well as providing an elongate shaft with the normal properties required for insertion thereof into a body passageway. The present invention therefore enables a catheter to be provided which addresses the aforementioned disadvantages of PVC based catheters leading to inter alia less wastage of starting materials and the possibility to use TV monitors for quality control.

While the background section of prior European patent application publication No. 0566755 (Cordis Corp.) makes it known that the use of a polyether block amide in the manufacture of medical device tubing intended for insertion into a body passageway is known per se, European patent application publication No. 0566755 goes on to teach that undesirable blooming develops in such tubing material after it has been stored for a length of time which can interfere with the adherence of a coating thereto, for example a coating for imparting lubricity to the tubing. The solution to the blooming problem according to European patent application publication No. 0566755 is to blend the polyether block amide with a polyetheramide component having substantially no ester linkages.

No such problem with adherence of the hydrophilic coating to a polyether block amide manifests itself when the method according to the present invention is followed despite the fact that blooming is sometimes observed after some months storage. This can be attributed to the manner in which the hydrophilic coating is applied to the elongate shaft in the method The polyether block amide used in the invention is believed to have a structure as follows:

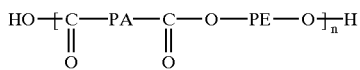

wherein PA is a polyamide, PE is a polyether and n is an integer greater than 1 which represents the number of blocks of copolymer molecular repeating units within the molecular formula of the copolymer. Representative polyether block amide materials include the Pebax® polymers (Elf Atochem S. A.).

In an embodiment of the invention the styrene block copolymer is a styrene-ethylene/butylene-styrene block copolymer, for example Evoprene® G (Evode Plastics Ltd.).

Application of the isocyanate solution to the elongate shaft surface results in a coating having unreacted isocyanate groups being formed on the elongate shaft surface. Application of the polyvinylpyrrolidone solution to the elongate shaft surface then results in a hydrophilic polyvinylpyrrolidone-polyurea interpolymer coating being formed on the elongate shaft surface. Curing of this hydrophilic coating binds the isocyanate compounds together to form a stable non-reactive network that binds the hydrophilic polyvinylpyrrolidone. To advantage, curing takes place in the presence of a water-containing gas, for example ambient air, to enable the isocyanate groups to react with the water to yield an amine which rapidly reacts with other isocyanate groups to form a urea cross-link.

In an embodiment of the invention the method further comprises the steps of evaporating the solvent of the isocyanate solution prior to application of the polyvinylpyrrolidone solution and evaporating the solvent of the polyvinylpyrrolidone solution prior to curing of the hydrophilic coating. This may for example be done by air drying.

In an embodiment of the invention the isocyanate compound comprises at least two unreacted isocyanate groups per molecule. The isocyanate may be selected from 2,4-toluene diisocyanate and 4,4'-diphenylmethane diisocyanate, or a pentamer of hexamethylene diisocyanate and toluene diisocyanate of cyanurate type, or trimerized hexamethylene diisocyanate biuret or mixtures thereof The solvent for the isocyanate compound is preferably one which does not react with isocyanate groups. The preferred solvent is methylene chloride but it is also possible to use ethyl acetate, acetone, chloroform, methyl ethyl ketone and ethylene dichloride, for example.

The isocyanate solution may advantageously contain between 0.5 to 10% (weight to volume) of the isocyanate compound, and may preferably contain between 1 to 6% (weight to volume) of the isocyanate compound. Generally, the isocyanate solution only needs to be in contact with the surface briefly, for example 5 to 60 sec.

To enhance adherence of the hydrophilic coating to the elongate shaft surface the elongate shaft may be swelled beforehand in a suitable solvent. Another way is to choose a solvent for the isocyanate solution which has the ability to swell or dissolve the elongate shaft surface which is to be coated.

In order to shorten the necessary reaction times and curing times suitable catalysts for isocyanate curing may be added. These catalysts may be dissolved in either the isocyanate solution or the polyvinylpyrrolidone solution but are preferably dissolved in the latter. Different types of amines are especially useful, for example diamines, but also for example triethylenediamine. Preferably, an aliphatic amine is employed which is volatisable at the drying and curing temperatures used for the coating, and which furthermore is non-toxic. Examples of suitable amines are N,N' diethylethylendiamine, hexamethylendiamine, ethylendiarnine, paradiaminobenzene, 1,3-propandiol-para-aminobenzoic acid diester and diaminobicyclo-octane.

Where the catalyst is in the polyvinylpyrrolidone solution, the proportion of catalyst in the solution is suitably between 0.1 to 50% by weight of the amount of polyvinylpyrrolidone, preferably between 0.1 to 10% by weight. Some of the above-mentioned amines, particularly the diamines, can also react with isocyanate and thereby contribute to the cross-linking of the isocyanate compounds that give the desired strong adherence between the hydrophilic coating and the polymer surface.

The polyvinylpyrrolidone used preferably has a mean molecular weight of between $10^4$ to $10^7$ with the most preferred mean molecular weight being about $10^5$. Polyvinylpyrrolidone having such a molecular weight is commercially available, for example under the trademark Kollidon® (BASF). Examples of suitable solvents for polyvinylpyrrolidone that may be used are methylene chloride (preferred), ethyl acetate, acetone, chloroform, methyl ethyl ketone and ethylene dichloride. The proportion of polyvinylpyrrolidone in the solution is preferably between 0.5 to 10% (weight to volume) and most preferred between 2 to 8% (weight to volume). The polyvinylpyrrolidone in the solvent is applied by dipping, spraying or the like for a short period of time, e.g. during 5 to 50 sec.

Curing of the coating is preferably performed at a temperature of 50 to 130° C., in for example an oven, for a duration of between 5 to 300 min.

According to the invention there is further provided a medical which presents a hydrophilic surface coated elongate shaft for insertion into a body passageway manufactured by the method according to the invention.

According to the invention there is yet further provided a medical device which presents an elongate shaft for insertion into a body passageway, the elongate shaft being made from a polyether block amide or a styrene block copolymer and provided with a hydrophilic outer surface coating formed from an interpenetrating network of polyvinylpyrrolidone and polyurea.

According to the invention there is additionally provided a medical device which presents an elongate shaft for insertion into a body passageway, the elongate shaft being made from a polyether block amide or a styrene block copolymer and provided with a polyvinylpyrrolidone hydrophilic outer surface coating having enhanced osmolality.

In an embodiment of the invention the hydrophilic coating contains an osmolality-increasing compound, for instance an inorganic salt selected from sodium and potassium chlorides, iodides, citrates and benzoates. The osmolality-increasing compound may be applied in the manner detailed in prior European patent application publication No. 0217771.

In an embodiment of the invention the medical device is a catheter, for example those designated for urological, angioplasty and valvuloplasty uses or the like. In this case, the polyether block amide or styrene block copolymer selected for the elongate shaft respectively has a hardness in the range 25 Sh D to 70 Sh D and 40 shore A to 70 shore D. Where the medical device is a urinary catheter a hardness in the range 25 Sh D to 45 Sh D for polyether block amide and 40 shore A to 45 shore D for styrene block copolymer is ideal with greater hardnesses being preferred for intravascular catheters.

According to the invention there is also provided the use of a styrene block copolymer in the manufacture of a medical device which presents an elongate shaft for insertion into a body passageway.

The invention will now be illustrated but not limited by the following examples.

EXAMPLE 1

A diisocyanate (named Desmodur IL) is dissolved in methylene chloride to a concentration of 2% (weight/volume). A urinary catheter formed exclusively or essentially exclusively from Pebax® (hereinafter a "urinary Pebax® catheter") with a hardness of 70 shore D is dipped in this solution for 15 seconds and is then dried at ambient temperature for 60 seconds. The catheter is then dipped for 1 second in a solution containing 6% (weight/volume) of polyvinylpyrrolidone (K90; mean molecular weight ~360 000) dissolved in methylene chloride. The catheter is then allowed to dry at ambient temperature for 60 seconds and is finally cured for 50 minutes at 100° C. The catheter is finally allowed to cool to room temperature and is then rinsed in water. The catheter has a slippery and adherent surface when wet.

The experiment was repeated with variations in the dipping time in the isocyanate bath ranging from 5 seconds to 1 minute, but no advantage was obtained by increasing the dipping time.

EXAMPLE 2

A diisocyanate (named Desmodur IL) is dissolved in ethyl acetate to a concentration of 2% (weight/volume). A urinary Pebax® catheter with a hardness of 35 shore D is dipped in this solution for 15 seconds and is then dried at ambient temperature for 60 seconds. The catheter is then dipped for 1 second in a solution containing 6% (weight/volume) of polyvinylpyrrolidone (K90; mean molecular weight ~360 000) dissolved in ethyl lactate (50%) and ethyl acetate (50%). The catheter is then allowed to dry at ambient temperature for 60 seconds and is finally cured for 50 minutes at 80° C. The catheter is finally allowed to cool to room temperature and is then rinsed in water. The catheter has a slippery and adherent surface when wet.

EXAMPLE 3

A diisocyanate (named Desmodur IL) is dissolved in methylene chloride (75%) and tri chloro ethylene (25%) to a concentration of 2% (weight/volume). A urinary Pebax® catheter with a hardness of 63 shore D is dipped in this solution for 15 seconds and is then dried at ambient temperature for 60 seconds. The catheter is then dipped for 1 second in a solution containing 6% (weight/volume) of polyvinylpyrrolidone (K90; mean molecular weight ~360 000) dissolved in methylene chloride (75%) and tri chloro ethylene (25%). The catheter is then allowed to dry at ambient temperature for 60 seconds and is finally cured for 50 minutes at 100° C. The catheter is finally allowed to cool to room temperature and is then rinsed in water. The catheter has a slippery and adherent surface when wet.

EXAMPLE 4

A diisocyanate (named Desmodur IL) is dissolved in ethyl acetate to a concentration of 2% (weight/volume). A urinary catheter manufactured from Evoprene® G with a hardness of 65 shore A is dipped in this solution for 15 seconds and is then dried at ambient temperature for 60 seconds. The catheter is then dipped for 1 second in a solution containing 6% (weight/volume) of polyvinylpyrrolidone (K90; mean molecular weight ~360 000) dissolved in methylene chloride. The catheter is then allowed to dry at ambient temperature for 60 seconds and is finally cured for 50 minutes at 100° C. The catheter is finally allowed to cool to room temperature and is then rinsed in water. The catheter has a slippery and adherent surface when wet.

The urinary catheters prepared according to the examples show low friction, good kink resistance, good dimension stability and possibility to be sterilised. Moreover, the longitudinal shrinkage of the catheters as a result of the coating process was less than 1% of the original length.

While the examples refer to the manufacture of urinary catheters it is to be understood that the invention is not restricted to this sole application but is equally applicable to other forms of catheters and moreover other constructions falling within the broad class of medical devices having an elongate shaft adapted for insertion into a body passageway as whole, for instance transurethral devices for treating erectile dysfunction and wound drains for insertion into body passageways in the form of wound cavities.

What is claimed is:

1. A method for the manufacture of a medical device comprising an elongate shaft, wherein the outer surface of the elongate shaft is coated with a stable hydrophilic coating for facilitating insertion of the elongate shaft into a body passageway, the method comprising the steps of:

a) forming the elongate shaft from a polyether block amide with a hardness in the range of 25 Sh D to 70 Sh D; and b) forming the hydrophilic coating on the elongate shaft by applying sequentially to the surface of the elongate shaft first a solution comprising between 0.05 to 40% (weight to volume) of an isocyanate compound and thereafter a solution containing between 0.5 and 50% (weight to volume) of polyvinylpyrrolidone and curing at an elevated temperature, wherein the hydrophilic coating on the elongate shaft presents a slippery and adherent surface when wet.

2. The method according to claim 1, wherein the isocyanate compound comprises at least two unreacted isocyanate groups per molecule.

3. The method according to claim 1 or 2, wherein the solvent of the isocyanate solution is an organic solvent which does not react with isocyanate.

4. The method according to claim 1 or 2, wherein the method further comprises the steps of evaporating the solvent of the isocyanate solution prior to application of the polyvinylpyrrolidone solution and evaporating the solvent of the polyvinylpyrrolidone solution prior to curing.

5. The method according to claim 1 or 2, wherein the curing is carried out in the presence of a water-containing gas.

6. The method according to claim 1 or 2, wherein the curing is cared out at a temperature of between about 50 and 130° C.

7. The method according to claim 1 or 2, wherein the isocyanate is selected from 2,4-toluene diisocyanate and 4,4'-diphenylmethane diisocyanate, or a pentamer of hexamethylene diisocyanate and toluene diisocyanate of cyanurate type, or trimerized hexamethylene diisocyanate biuret or mixtures thereof.

8. The method according to claim 1 or 2, wherein the method comprises the steps of applying to the hydrophilic coating a solution containing an osmolality-increasing compound and evaporating the solution containing the osmolality-increasing compound.

9. The method according to claim 8, wherein the osmolality-increasing compound is an inorganic salt selected from sodium and potassium chlorides, iodides, citrates and benzoates.

10. A medical device which presents a hydrophilic surface coated elongate shaft for insertion into a body passageway manufactured by the method according to claim 1.

11. A medical device comprising an elongate shaft for insertion into a body passageway, wherein the elongate shaft is made from a polyether block amide with a hardness in the range of 25 Sh D to 70 Sh D, and the outer surface of the elongate shaft is coated with a stable hydrophilic coating formed from an interpenetrating network of polyvinylpyrrolidone and polyurea, and wherein the hydrophilic coating on the elongate shaft presents a slippery and adherent surface when wet.

12. The medical device according to claim 11, wherein the hydrophilic coating contains an osmolality-increasing compound.

13. The medical device according to claim 12, wherein the osmolality-increasing compound is an inorganic salt selected from sodium and potassium chlorides, iodides, citrates and benzoates.

14. The medical device according to any one of claims 10 or 11, wherein the device is a catheter.

15. The medical device according to claim 14, wherein the device is a urinary catheter.

* * * * *